(12) United States Patent  (10) Patent No.: US 8,035,685 B2
Jensen  (45) Date of Patent: Oct. 11, 2011

(54) SYSTEMS AND METHODS FOR COMMUNICATING VIDEO DATA BETWEEN A MOBILE IMAGING SYSTEM AND A FIXED MONITOR SYSTEM

(75) Inventor: Vernon Thomas Jensen, Draper, UT (US)

(73) Assignee: General Electric Company, Schenectady, NY (US)

( * ) Notice: Subject to any disclaimer, the term of this patent is extended or adjusted under 35 U.S.C. 154(b) by 1106 days.

(21) Appl. No.: 11/830,211

(22) Filed: Jul. 30, 2007

(65) Prior Publication Data

US 2009/0033742 A1  Feb. 5, 2009

(51) Int. Cl.
*H04N 7/18* (2006.01)
*A61B 1/04* (2006.01)

(52) U.S. Cl. .................. 348/77; 348/73; 348/74; 348/75

(58) Field of Classification Search .................... 348/45, 348/61, 65–80
See application file for complete search history.

(56) References Cited

U.S. PATENT DOCUMENTS

| 5,729,584 | A | 3/1998 | Moorman et al. | |
|---|---|---|---|---|
| 5,751,785 | A | 5/1998 | Moorman et al. | |
| 6,666,579 | B2 | 12/2003 | Jensen | |
| 6,697,664 | B2 | 2/2004 | Kienzle, III et al. | |
| 7,116,812 | B2 | 10/2006 | Langan et al. | |
| 7,343,036 | B2 | 3/2008 | Kleen et al. | |
| 7,400,752 | B2 * | 7/2008 | Zacharias | 382/128 |
| 7,593,507 | B2 * | 9/2009 | Ohta et al. | 378/98.8 |
| 7,613,478 | B2 * | 11/2009 | Jabri et al. | 455/556.1 |
| 7,756,563 | B2 | 7/2010 | Higgins et al. | |
| 2001/0055061 | A1 * | 12/2001 | Onishi et al. | 348/65 |
| 2004/0030367 | A1 * | 2/2004 | Yamaki et al. | 607/60 |
| 2004/0264754 | A1 | 12/2004 | Kleen et al. | |
| 2005/0009574 | A1 * | 1/2005 | Lin | 455/569.2 |
| 2005/0179538 | A1 * | 8/2005 | Morita et al. | 340/539.1 |
| 2007/0122783 | A1 | 5/2007 | Habashi | |
| 2007/0156017 | A1 * | 7/2007 | Lamprecht et al. | 600/102 |
| 2008/0252778 | A1 * | 10/2008 | Dunki-Jacobs | 348/441 |
| 2009/0032744 | A1 * | 2/2009 | Kito et al. | 250/580 |
| 2009/0192519 | A1 * | 7/2009 | Omori | 606/130 |

FOREIGN PATENT DOCUMENTS

| EP | 1649812 | 4/2006 |
|---|---|---|
| EP | 1769728 | 4/2007 |
| WO | WO2008115312 | 9/2008 |

* cited by examiner

*Primary Examiner* — Joshua Joo
(74) *Attorney, Agent, or Firm* — Armstrong Teasdale LLP

(57) ABSTRACT

A system for communicating video data is described. The system includes a mobile imaging system, at least one monitor fixed to a room in a medical facility, and a video transmitter assembly coupled to the mobile imaging system to transmit a video signal. The system for communicating video data also includes a video receiver assembly coupled to the at least one monitor to receive the video signal and display the video signal on the at least one monitor.

14 Claims, 4 Drawing Sheets

US 8,035,685 B2

SYSTEMS AND METHODS FOR COMMUNICATING VIDEO DATA BETWEEN A MOBILE IMAGING SYSTEM AND A FIXED MONITOR SYSTEM

BACKGROUND OF THE INVENTION

This invention relates generally to transfer of data, and more particularly to systems and methods for communicating video data between a mobile imaging system and a fixed monitor system.

Mobile C-arms and other imaging and patient monitoring devices are used extensively in operating rooms (OR), Radiology departments, outpatient clinics, and Cardiac and Vascular intervention suites. Moreover, most modern hospitals and clinics have a wall mounted or ceiling mounted video monitor built-in. A plurality of non-mobile imaging systems are "hard wired" as one of a plurality of video sources to the built-in monitor.

However, the mobile C-arms and navigation systems are less frequently plugged into the built-in monitor because of an inconvenience of manually connecting and disconnecting a video feed to the built-in monitor, of an inconvenience of making any video system adjustments for displaying a video signal on the built-in monitor, or of a potential for video signal incompatibilities between the mobile C-arms and the built-in monitor.

BRIEF DESCRIPTION OF THE INVENTION

FIG. 1 is an isometric view of a system including a mobile navigation system and a mobile imaging system.

FIG. 2 is an exemplary block diagram of an embodiment of an integrated mobile imaging navigation system.

FIG. 3 is a top view of an embodiment of a system for communicating video data between a mobile imaging system and a fixed monitor system.

FIG. 4 is a flowchart of an embodiment of a method for communicating video data between a mobile imaging system and a fixed monitor system

BRIEF DESCRIPTION OF THE DRAWINGS

In one aspect, a system for communicating video data is described. The system includes a mobile imaging system, at least one monitor fixed to a room in a medical facility, and a video transmitter assembly coupled to the mobile imaging system to transmit a video signal. The system for communicating video data also includes a video receiver assembly coupled to the at least one monitor to receive the video signal and display the video signal on the at least one monitor.

In another aspect, a system for communicating video data is described. The system includes a mobile navigation system, at least one monitor fixed to a room in a medical facility, and a video transmitter assembly coupled to the mobile navigation system to transmit a video signal. The system for communicating video data further includes a video receiver assembly coupled to the at least one monitor to receive the video signal and display the video signal on the at least one monitor.

In yet another aspect, a system for communicating video data is described. The system includes an integrated mobile imaging navigation system, at least one monitor fixed to a room in a medical facility, and a video transmitter assembly coupled to the integrated mobile imaging navigation system to transmit a video signal. The system for communicating video data further includes a video receiver assembly coupled to the at least one monitor to receive the video signal and display the video signal on the at least one monitor.

DETAILED DESCRIPTION OF THE INVENTION

Figure 1:
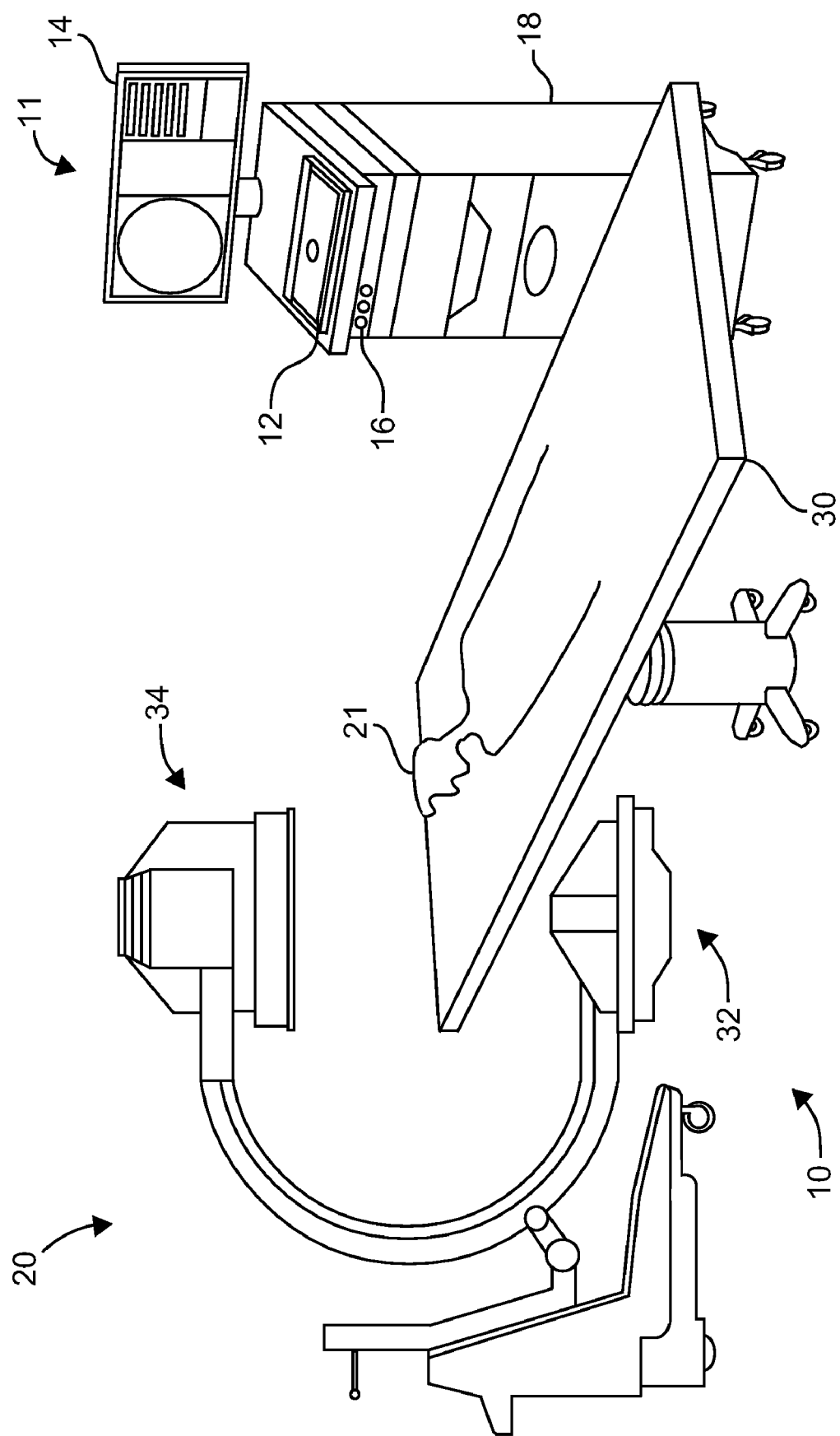

FIG. 1 is an isometric view of an embodiment of a system 10 including a mobile navigation system 11. System 10 is located within a room, such as a room within a medical facility. Examples of the room within the medical facility include a room within hospital, a room within a physician's clinic, an operating room, a cardiac and vascular intervention suite, and a room within a radiology department. The mobile navigation system 11 includes a portable computer 12, at least one display 14, and a navigation interface 16 on a portable cart 18.

System 10 further includes a mobile imaging system 20, which is a fluoroscopic imaging system including a C-arm assembly used to generate x-ray images of a patient 21 supported on a table 30. In another embodiment, an O-arm assembly, a computed tomography system, an ultrasound imaging system, or an endoscopic imaging system is included within a mobile imaging system to acquire a medical image of patient 21. Mobile imaging system 20 includes a source 32 that generates x-rays upon activation. The x-rays pass through patient 21. A detector 34 of the mobile imaging system 20 detects a portion of the x-rays to generate a plurality of signals. Under control of a processor of the mobile imaging system 20, the signals generated by the detector 34 are converted into video signals and displayed as a video medical image of patient 21 on at least one display 14 within the room.

System 10 also includes at least one electromagnetic field generator that may be attached to surgical device and that is a part of the mobile navigation system 11. Examples of the surgical device include a surgical instrument, such as a catheter or a guidewire, and a surgical implant, such as a screw or a rod. The mobile navigation system 11 further includes at least one electromagnetic field sensor. The at least one electromagnetic field generator generates electromagnetic field signals that are detected by the at least one electromagnetic sensor that may be attached to table 30. The electromagnetic field signals are digitized by electronics within the at least one electromagnetic field sensor and the digitized signals are transmitted via a wired or a wireless connection to navigation interface 16 of mobile navigation system 11. The mobile navigation system 11 calculates a location of the surgical device. Under the control of a processor, such as a processor within computer 12, the location of the surgical device is displayed as a video image on the at least one display 14. In another embodiment, the mobile navigation system 11 and a mobile imaging system, such as mobile imaging system 20, O-arm assembly, computed tomography system, ultrasound imaging system, or endoscopic imaging system are integrated to form an integrated mobile imaging navigation system.

Figure 2:
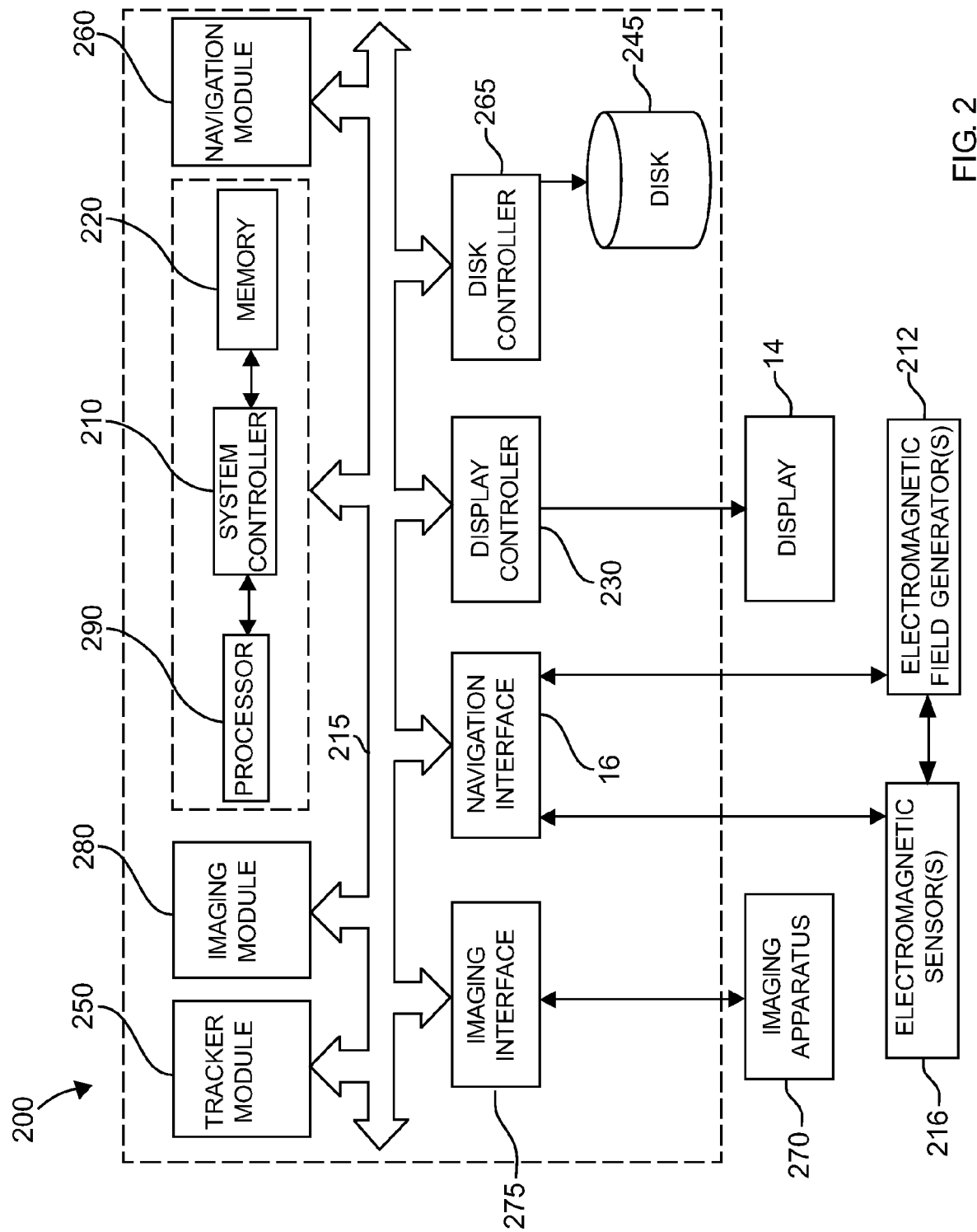

FIG. 2 is an exemplary block diagram of an embodiment of an integrated mobile imaging navigation system 200. System 200 includes the at least one display 14, the navigation interface 16, a system controller 210, at least one electromagnetic field generator 212, a local interface 215, at least one electromagnetic field sensor 216, a memory 220, a display controller 230, a tracker module 250, a navigation module 260, a disk controller 265, an imaging apparatus 270, an imaging interface 275, an imaging module 280, and a processor 290. The imaging apparatus 270, the imaging interface 275, the local interface 215, the imaging module 280, the processor 290, system controller 210, memory 220, display controller 230, display 14, disk controller 265, and disk 245 are parts of a mobile imaging system. Moreover, the at least one electromagnetic field sensor 216, the at least one electromagnetic field generator 212, the navigation interface 16, the local interface 215, the tracker module 250, the navigation module 260, the processor 290, system controller 210, memory 220, display controller 230, display 14, disk controller 265, and disk 245 are parts of a mobile navigation system. As used herein, the term controller is not limited to just those integrated circuits referred to in the art as a controller, but broadly refers to a processor, a computer, a microcontroller, a microcomputer, a programmable logic controller, an application specific integrated circuit, and any other programmable circuit.

The integrated mobile imaging navigation system 200 is illustrated conceptually as including a collection of modules, but may be implemented using any combination of dedicated hardware boards, digital signal processors, field programmable gate arrays, and processors. Alternatively, the modules may be implemented using an off-the-shelf computer with a single processor or multiple processors, with the functional operations distributed between the processors. As an example, it may be desirable to have a dedicated processor for position information calculations as well as a dedicated processor for display operations. As a further option, the modules may be implemented using a hybrid configuration in which certain modular functions are performed using dedicated hardware, while the remaining modular functions are performed using an off-the-shelf computer. Memory 220 may be an optical memory, a flash memory, or a magnetic memory. The operations of the modules may be controlled by system controller 210.

The at least one electromagnetic field generator 212 is coupled to navigation interface 16. The at least one electromagnetic field generator 212 generates at least one electromagnetic field that is detected by the at least one electromagnetic sensor 216.

The navigation interface 16 receives digitized signals from the at least one electromagnetic field sensor 216. The digitized signals received by the navigation interface 16 represent magnetic field information of the electromagnetic field generated by the at least one electromagnetic field generator 212 and detected by the at least one electromagnetic field sensor 216. In the embodiment illustrated in FIG. 2, the navigation interface 16 transmits the digitized signals to a tracker module 250 over local interface 215, such as a peripheral component interconnect (PCI) bus. According to various alternate embodiments, various equivalent bus technologies may be substituted. The tracker module 250 calculates a position of the surgical device from the digitized signals.

The position of the surgical device is stored by system controller 210 in memory 220 and/or by the disk controller 265 into disk 245. The disk 245 and the memory 220 are examples of a computer-readable medium. By way of example only, the disk 245 is a hard disk but other suitable storage devices may be used. The disk controller 265 retrieves data from and stores data on disk 245.

Imaging apparatus 270 is activated to acquire patient data, such as, x-ray data, computed tomography data, ultrasound data, or endoscopic data, of patient 21. Imaging interface 275 receives the patient data from imaging apparatus 270 and communicates the patient data to imaging module 280 and navigation module 260. Navigation module 260 works in conjunction with imaging module 280 to register the position of the surgical device to the acquired patient data and generates video image data suitable to visualize the patient data and the position of the surgical device. The patient data is stored by system controller 210 in memory 220 and/or by the disk controller 265 into disk 245. In another embodiment, the navigation module 260 and the imaging module 280 are integrated into one module.

Display controller 265 receives the video image data from the navigation module 260 via local interface 215 and displays the video image data as video images on the at least one display 14. The video images may be stored by system controller 210 in memory 220 and/or by the disk controller 265 into disk 245.

Figure 3:
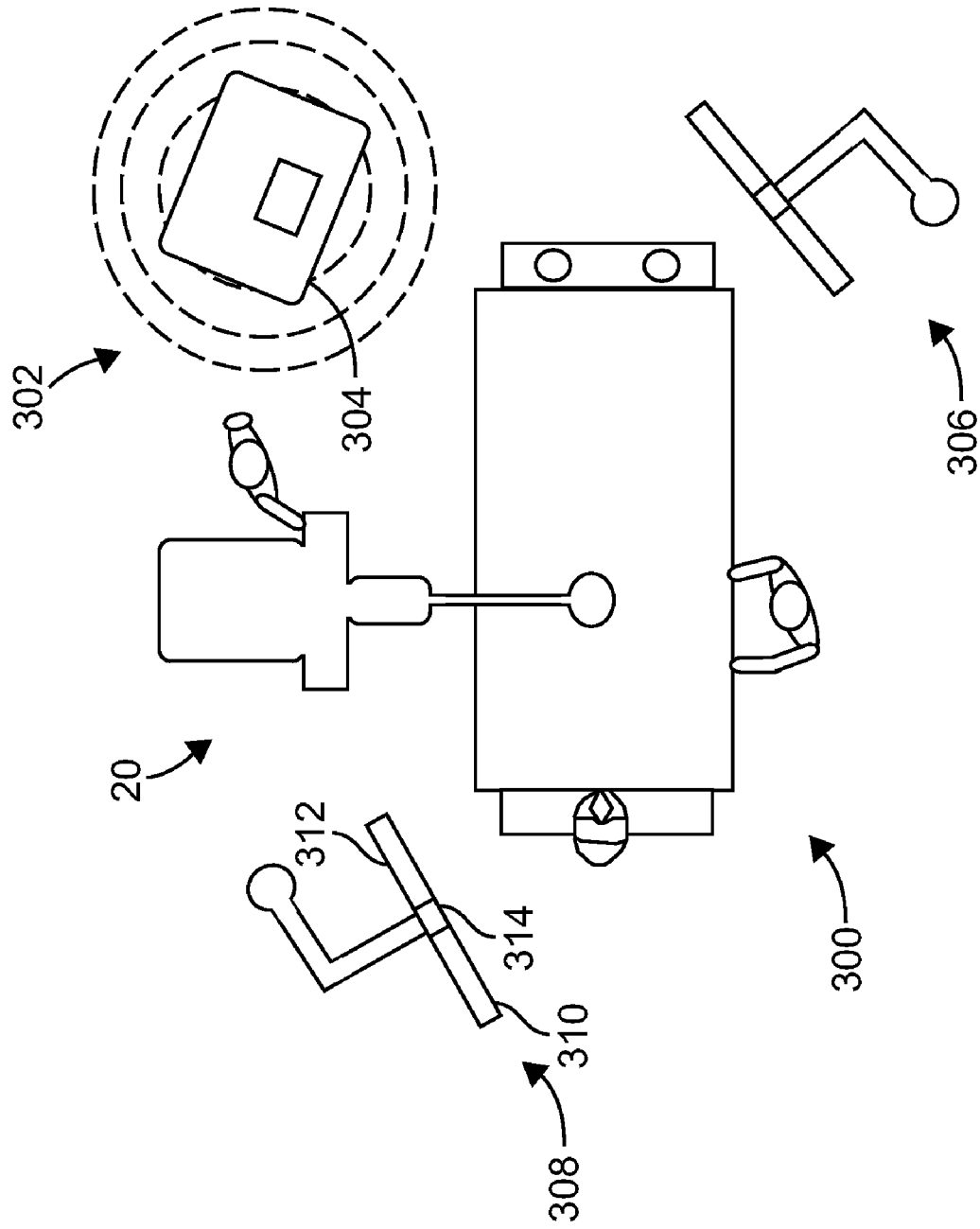

FIG. 3 is a top view of an embodiment of a system 300 for communicating video data between a mobile imaging system and a fixed monitor system. System 300 is located within the room. System 300 includes the mobile imaging system 20 and a mobile navigation system 302. The mobile navigation system 302 includes mobile navigation system 11 shown in the embodiment of FIG. 1 and further includes a wireless video transmitter assembly 304. In another embodiment, an integrated mobile imaging navigation system is used instead of the mobile navigation system 11.

System 300 further includes a single built-in monitor 306 and a dual built-in monitor 308. Each of the single built-in monitor 306 and the dual built-in monitor 308 are affixed to a portion, such as a ceiling or a wall, of the room. The dual built-in monitor includes a monitor 310 and a monitor 312. In another embodiment, system 300 includes a triple or a quadruple built-in monitor. In yet another embodiment, system 300 includes any number of built-in monitors.

The dual built-in monitor 308 includes a wireless video receiver assembly 314. In another embodiment, single built-in monitor 306 includes wireless video receiver assembly 314. In yet another embodiment, system 300 includes any number of wireless video receiver assemblies and any number of wireless video transmitter assemblies.

Figure 4:
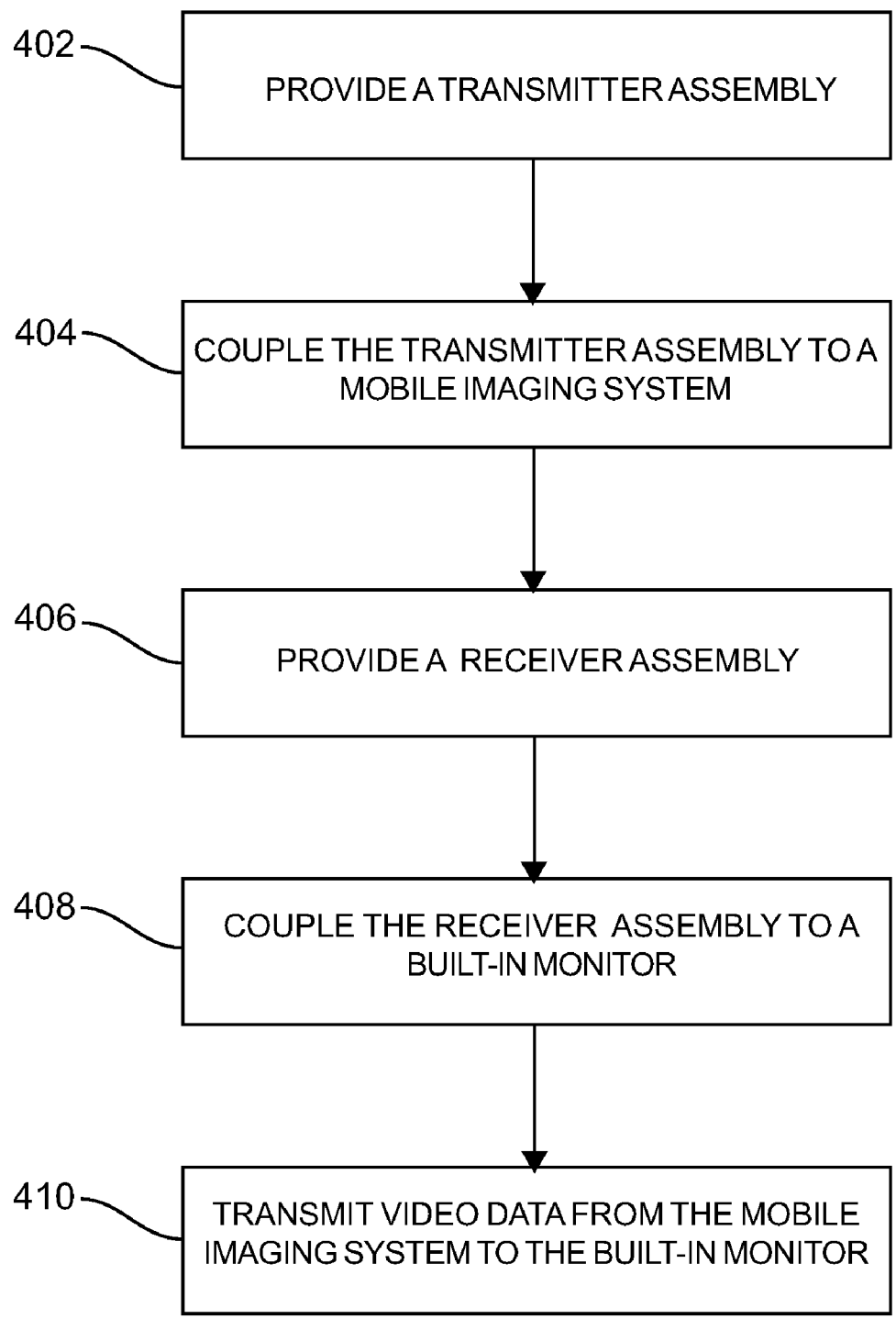

FIG. 4 is a flowchart of an embodiment of a method for communicating video data between a mobile imaging system and a fixed monitor system. The method includes providing 402 the wireless video transmitter assembly 304 and coupling 404 the wireless video transmitter assembly 304 to a mobile imaging system, such as mobile imaging system 20, an ultrasound imaging system, a computed tomography system, an endoscopic imaging system, or an imaging system including an O-arm assembly. In another embodiment, transmitter assembly 304 is integrated within mobile navigation system 11, such as within cart 18 of mobile navigation system 11, or within the integrated mobile imaging navigation system 200, such as within a cart of the integrated mobile imaging navigation system 200. In yet another embodiment, wireless video transmitter assembly 304 is a stand-alone transmitter assembly not integrated within a mobile imaging system, a mobile navigation system, or an integrated mobile imaging navigation system. A power supply is integrated within the wireless video transmitter assembly 304. Optionally, the power supply may not be integrated within the wireless video transmitter assembly 304. The wireless video transmitter assembly 304 includes a wireless video transmitter having one or more input ports.

The method further includes providing 406 the wireless video receiver assembly 314 and coupling 408 the wireless video receiver assembly 314 to a built-in monitor. For example, the wireless video receiver assembly 314 may be electrically connected to the single built-in monitor 306 and the wireless video receiver assembly 314 is also electrically connected to dual built-in monitor 308. Each wireless video receiver assembly 314 includes a wireless video receiver having one or more video output ports.

The wireless video transmitter assembly 304 receives video data, such as video image data, from at least one of the mobile imaging system 20, mobile navigation system 11, the integrated mobile imaging navigation system 200, an ultrasound imaging system, a computed tomography system, an endoscopic imaging system, a video cassette recorder (VCR), and a digital video disc (DVD) player.

Video data is transmitted 410 in the form of video signals from the wireless transmitter assembly 304 to at least one wireless video receiver assembly 314 of a built-in monitor. For example, video image data is transmitted from the wireless video transmitter assembly 304 of the mobile navigation system 302 to the wireless video receiver assembly 314 of the dual built-in monitor 308. Under control of a processor within the wireless video receiver assembly 314, video images representing the video image data from the wireless video transmitter assembly 304 are generated and displayed on the dual built-in monitor 308. As another example, video image data is transmitted from the wireless video transmitter assembly 304 to the wireless video receiver assembly 314 of the built-in monitor 306. Under control of a processor within the wireless video receiver assembly 314 of the built-in monitor 306, video images representing the video image data from the wireless video transmitter assembly 304 are displayed on the built-in monitor 306.

Under the control of a processor within the wireless video receiver assembly 314, video data received from the wireless video transmitter assembly 304 is output via the one or more video output ports of the wireless video receiver assembly 314. For example, one of the video output ports of the wireless video receiver assembly 314 of dual built-in monitor 308 provides video data to the monitor 310 of the dual built-in monitor 308 and another one of the video output ports of the wireless video receiver assembly 314 of the dual built-in monitor 308 provides the same or different video data to the monitor 312 of the dual built-in monitor 308. The different video data that may be provided to the monitor 312 of the dual built-in monitor 308 is obtained from a different system that video data provided to the monitor 310 of the dual built-in monitor 308. For example, the different video data provided to monitor 312 for display is obtained from mobile imaging assembly 20 and video data provided to monitor 310 is obtained from an ultrasound imaging system, the VCR, the DVD player, the computed tomography system, or the endoscopic imaging system. Similarly, a third video source of video images different than video images displayed on monitors 310 and 312 is displayed on built-in monitor 306.

In one embodiment, one of the output ports of the wireless video receiver assembly 314 of the dual built-in monitor 308 is connected to monitor 310 of the dual built-in monitor 308 to display video images in a different format than a format of displaying video images on monitor 312 of the dual built-in monitor 308. In this embodiment, video images displayed on monitor 310 in the different format are generated from video data received from an output port of the wireless video receiver assembly 314 that is different from an output port of the receiver assembly 314 providing video data for display on monitor 312. As an example, the different format of displaying video images on monitor 310 of the dual built-in monitor 308 is National Television Systems Committee (NTSC) format if video images displayed on monitor 312 of the dual built-in monitor 308 have phase alternation line (PAL) or Sequential Couleur Avec Memoire (SECAM) format. In another embodiment, video images representing video data received from wireless video receiver assembly 314 are displayed on monitor 310, 312, or built-in monitor 306 in an NTSC, PAL, RGB, SECAM, composite, analog, or digital video standard. It is noted that if any of the built-in monitor 302, the monitor 310, and the monitor 312 detects and displays video images of multiple display formats, the wireless video receiver assembly 314 has fewer video output ports than a number of video output ports when the monitor does not detect and display video images of multiple display formats.

In yet another embodiment, the wireless video receiver assembly 314 includes one or more feed-through inputs that receive a hardwire video data input of video data from at least one of a mobile imaging system, a mobile navigation system, and an integrated mobile imaging navigation system. The hardwire video data input is not received from the wireless video transmitter assembly 304. The wireless video receiver assembly 314 does not demodulate video data received via the hardwire video data input. In the embodiment, the wireless video transmitter assembly 304 includes an activation button. When a user selects the activation button, the wireless video transmitter assembly 304 sends a signal to activate the wireless video receiver assembly 314. Upon activation under the control of a processor within the wireless video receiver assembly 314, the wireless video receiver assembly 314, under control of the processor, switches from receiving video data via the hardwire video data input to wirelessly receiving video data from wireless video transmitter assembly 304. Further, in the embodiment, when there is no acquisition of patient data by scanning patient 21, or when a sensor, such as detector 34, of mobile imaging system 20 is inactive, under control of a processor, such as system controller 210, within wireless video transmitter assembly 302, the transmitter of the transmitter assembly 302 sends a signal to the wireless video receiver assembly 314 to switch to receive data from the hardwire video data input instead of receiving video data from the wireless video transmission assembly 304.

In another embodiment, the wireless video transmitter assembly 304 includes a video input switching button. When a user selects the video input switching button, under control of a processor, such as system controller 210, the wireless video transmitter assembly 304 switches from transmitting video data from one of mobile imaging system 20, mobile navigation system 11, integrated mobile imaging navigation system 200, ultrasound imaging system, endoscopic imaging system, computed tomography system, and an O-arm imaging system to transmitting video data from one of the remaining of mobile imaging system 20, mobile navigation system 11, integrated mobile imaging navigation system 200, ultrasound imaging system, endoscopic imaging system, computed tomography system, and an O-arm imaging system. Upon selection of the video input switching button, the wireless video receiver assembly 308 receives a video signal from the one of the remaining of mobile imaging system 20, mobile navigation system 11, integrated mobile imaging navigation system 200, ultrasound imaging system, endoscopic imaging system, computed tomography system, and an O-arm imaging system.

In yet another embodiment, the wireless video receiver assembly 314 of the built-in monitor 306 receives video data from the wireless video transmitter assembly 304 that has received the video data from the VCR or a digital imaging and communications in medicine (DICOM) compliant video capture device. In the embodiment, the wireless video receiver assembly 314 of the dual built-in monitor 308 receives video data from the wireless video transmitter assembly 304 that has received the video data from a VCR different than the VCR from which video data is displayed on the built-in monitor 306. In another embodiment, the wireless video receiver assembly 314 of the dual built-in monitor 308 receives video data from the wireless video transmitter assembly 304 that has received the video data from a DICOM compliant device different than the DICOM compliant device from which video data is displayed on the built-in monitor 306.

In another embodiment, the wireless video receiver assembly 314 detects proximity of the wireless video transmitter assembly 304 or another wireless video transmitter assembly, similar to the wireless video transmitter assembly 304, within the room and switches between video inputs automatically. For example, when the wireless video receiver of the wireless video receiver assembly 314 of built-in monitor 306 is closer to wireless video transmitter assembly 314 compared to a wireless video transmitter assembly, similar to the transmitter assembly 314, within the room, the receiver assembly 314 receives video data from the transmitter assembly 314 and does not receive video data from the other transmitter assembly. As another example, when the wireless video signal receiver of the wireless video signal receiver assembly 314 of built-in monitor 306 is closer to a wireless video transmitter assembly, similar to wireless video transmitter assembly 314, within the room than to transmitter assembly 314, the wireless video signal receiver receives video data from the transmitter assembly similar to transmitter assembly 314 and does not receive video data from transmitter assembly 314.

It is noted that in another embodiment, the wireless video receiver assembly 314 is a stand-alone receiver assembly that receives power from a power supply not integrated within the receiver assembly. In yet another embodiment, the wireless video transmitter assembly 304 includes a video switcher, a scan converter, and/or a video memory that allows flexible video reformatting, such as zoom, pan, X-to-1 reformatting, picture-in-picture, of video data.

Technical effects of the herein described systems and methods for communicating video data between a mobile imaging system and a fixed monitor system include wirelessly transmitting video data from the wireless video transmitter assembly 304 to the wireless video receiver assembly 314. The wireless transmission avoids a need for a surgeon or a radiologist, within the room, to manually connect, via a wired connection, at least one of the mobile imaging system 20, the mobile navigation system 11, an ultrasound imaging system, an endoscopic imaging system, a computed tomography system, and the integrated mobile imaging navigation system 200 with either built-in monitor 306 or the dual built-in monitor 308. Furthermore, an automatic or a semi-automatic connection between a mobile imaging system, a mobile navigation system, or an integrated mobile imaging navigation system is enabled to allow switching between the hardwire video data input and wireless video data input. Moreover, other technical effects include switching between the hardwire video data input and the video data wirelessly received from the wireless video transmitter assembly 304. Yet other technical effects include providing wireless video receiver assembly 314 that accommodates multiple monitors or multiple display format standards. Other technical effects include switching between video data received from wireless video transmitter assembly 304 and another wireless video transmitter assembly based on proximity.

While the invention has been described in terms of various specific embodiments, those skilled in the art will recognize that the invention can be practiced with modification within the spirit and scope of the claims.

What is claimed is:

1. A system for communicating video data, said system comprising:
    a mobile imaging system;
    at least one monitor fixed to a room in a medical facility;
    a video transmitter assembly coupled to said mobile imaging system to transmit a video signal; and
    a wireless video receiver assembly coupled to the at least one monitor to receive the video signal and display the video signal on said at least one monitor,
    said video transmitter assembly configured to send an activation signal to activate said wireless video receiver assembly, wherein said wireless video receiver assembly switches from a wired connection to receiving a video signal from said video transmitter assembly upon receiving the activation signal, wherein said wireless video receiver assembly switches from receiving a video signal from said video transmitter assembly to receiving a video signal from the wired connection upon receiving a determination that said mobile imaging system is not used to acquire data from a patient.

2. The system in accordance with claim 1, wherein said wireless video receiver assembly receives a video signal from said video transmitter assembly based on a proximity of said video transmitter assembly to said wireless video receiver assembly relative to a proximity of said wireless video receiver assembly with respect to another video transmitter assembly.

3. The system in accordance with claim 1, wherein said mobile imaging system includes one of a C-arm assembly, an ultrasound imaging system, an endoscopic imaging system, and a computed tomography system.

4. The system in accordance with claim 1, wherein said wireless video receiver assembly includes an input to receive a video signal via a wired connection.

5. The system in accordance with claim 1, wherein said video transmitter assembly is configured to receive a video signal from said mobile imaging system and another video signal from a recorder.

6. A system for communicating video data, said system comprising:
    a mobile navigation system;
    at least one monitor fixed to a room in a medical facility;
    a video transmitter assembly coupled to said mobile navigation system to transmit a video signal; and
    a wireless video receiver assembly coupled to the at least one monitor to receive the video signal and display the video signal on said at least one monitor,
    said video transmitter assembly configured to send an activation signal to activate said wireless video receiver assembly, wherein said wireless video receiver assembly switches from a wired connection to receiving a video signal from said video transmitter assembly upon receiving the activation signal, wherein said wireless video receiver assembly switches from receiving a video signal from said video transmitter assembly to receiving a video signal from the wired connection upon receiving a determination that said mobile navigation system is not used to acquire data from a patient.

7. The system in accordance with claim 6, wherein said wireless video receiver assembly receives a video signal from said video transmitter assembly based on a proximity of said video transmitter assembly to said wireless video receiver assembly relative to a proximity of said wireless video receiver assembly with respect to another video transmitter assembly.

8. The system in accordance with claim 6, wherein said mobile navigation system is configured to generate a position of a surgical device.

9. The system in accordance with claim 6, wherein said wireless video receiver assembly includes an input to receive a video signal via a wired connection.

10. The system in accordance with claim 6, wherein said video transmitter assembly is configured to receive a video signal from said mobile navigation system and another video signal from a recorder.

11. A system for communicating video data, said system comprising:
   an integrated mobile imaging navigation system;
   at least one monitor fixed to a room in a medical facility;
   a video transmitter assembly coupled to said integrated mobile imaging navigation system to transmit a video signal; and
   a wireless video receiver assembly coupled to the at least one monitor to receive the video signal and display the video signal on said at least one monitor,
   said video transmitter assembly is configured to send an activation signal to activate said wireless video receiver assembly, wherein said wireless video receiver assembly switches from a wired connection to receiving a video signal from said video transmitter assembly upon receiving the activation signal, wherein said wireless video receiver assembly switches from receiving a video signal from said video transmitter assembly to receiving a video signal from the wired connection upon receiving a determination that said integrated mobile imaging navigation system is not used to acquire data from a patient.

12. The system in accordance with claim 11, wherein said wireless video receiver assembly receives a video signal from said video transmitter assembly based on a proximity of said video transmitter assembly to said wireless video receiver assembly relative to a proximity of said wireless video receiver assembly with respect to another video transmitter assembly.

13. The system in accordance with claim 11, wherein said integrated mobile imaging navigation system includes an imaging system and a navigation system, wherein the imaging system includes one of a C-arm assembly, an ultrasound imaging system, an endoscopic imaging system, and a computed tomography system.

14. The system in accordance with claim 11, wherein said wireless video receiver assembly includes an input to receive a video signal via a wired connection.

* * * * *